United States Patent [19]

Yokota et al.

[11] Patent Number: 4,476,304

[45] Date of Patent: Oct. 9, 1984

[54] PROCESS FOR THE PURIFICATION OF RIBOFLAVINE-5'-MONOPHOSPHATE

[75] Inventors: Kenji Yokota, Tokyo; Hiroshi Kusano, Kanagawa; Ryuichi Sugimoto, Tokyo, all of Japan

[73] Assignees: Mitsubishi Chemical Industries Limited; Wakamoto Pharmaceutical Co., Ltd., both of Japan

[21] Appl. No.: 409,809

[22] Filed: Aug. 20, 1982

[30] Foreign Application Priority Data

Aug. 21, 1981 [JP] Japan ................. 56-131355

[51] Int. Cl.$^3$ .............................. C07F 9/65
[52] U.S. Cl. .......................... 544/244; 544/251
[58] Field of Search .................... 544/244, 251

[56] References Cited

PUBLICATIONS

Sun, et al., Canadian J. Chem., vol. 43, pp. 969–976, (1965).
Mengoli, et al., Nature, vol. 212, No. 5061, pp. 481–483, (10/29/66).
Cerletti, et al., Chemical Abstracts, vol. 52, 14082a, (1958); vol. 53, 10359g, (1959).
Ukita, et al., Chemical Abstracts, vol. 55, 10455g, (1961).
Kobayshi, et al., Chemical Abstracts, vol. 62, 757b, (1965).
Fujii, Chemical Abstracts, vol. 76, 158330m, (1972).
Betto, et al., Chemical Abstracts, vol. 84, 118007v, (1976).

Primary Examiner—Donald G. Daus
Assistant Examiner—Diana G. Rivers
Attorney, Agent, or Firm—Sughrue, Mion, Zinn, Macpeak and Seas

[57] ABSTRACT

A process for the purification of riboflavine-5'-monophosphate comprising subjecting crude riboflavine-5'-monophosphate to chromatography using a column packed with a weakly basic anion-exchange resin having a skeleton of a crosslinked polyacrylic acid ester or polymethacrylic acid ester in which at least a part of the ester linkages thereof are converted into amide linkages represented by the following formula (1):

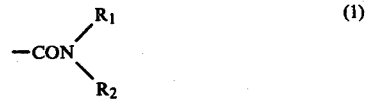

to obtain a fraction of riboflavine-5'-monophosphate containing a reduced amount of impurities from an eluate of the column is disclosed.

10 Claims, 3 Drawing Figures

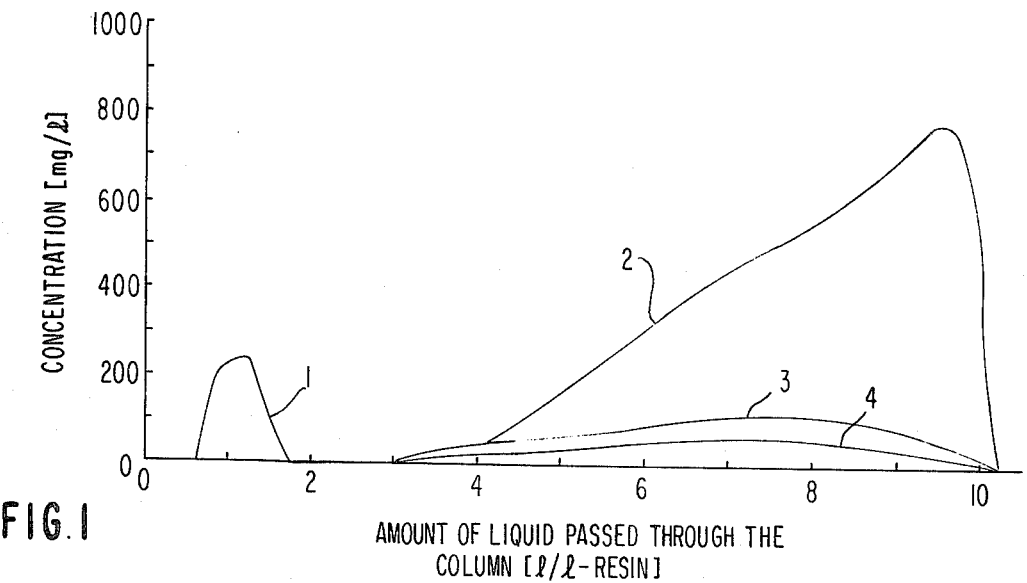
FIG.1 AMOUNT OF LIQUID PASSED THROUGH THE COLUMN [ℓ/ℓ-RESIN]
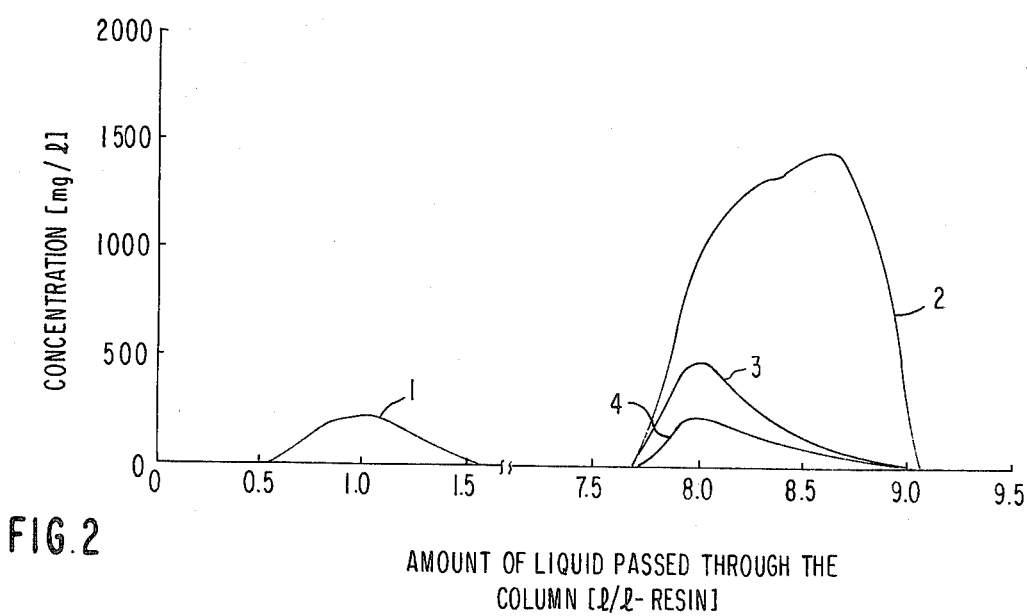
FIG.2 AMOUNT OF LIQUID PASSED THROUGH THE COLUMN [ℓ/ℓ-RESIN]
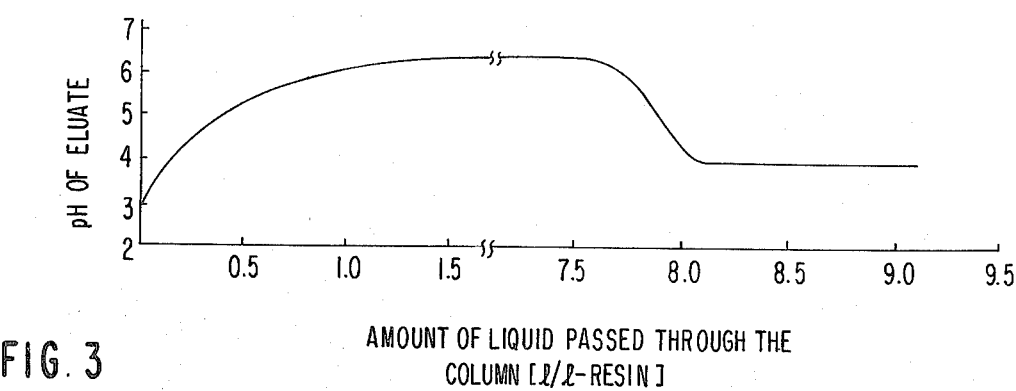
FIG.3 AMOUNT OF LIQUID PASSED THROUGH THE COLUMN [ℓ/ℓ-RESIN]

PROCESS FOR THE PURIFICATION OF RIBOFLAVINE-5'-MONOPHOSPHATE

FIELD OF THE INVENTION

The present invention relates to a process for the purification of riboflavine-5'-monophosphate (hereinafter referred to as 5'-FMN). More particularly, the present invention relates to a process for obtaining 5'-FMN containing a reduced amount of impurities from crude 5'-FMN containing impurities such as riboflavine, riboflavine-4'-monophosphate (hereinafter referred to as 4'-FMN), a riboflavine polyphosphoric acid ester, and other riboflavine derivatives.

BACKGROUND OF THE INVENTION

5'-FMN is a compound which plays a quite vital role as a coenzyme for various enzyme reactions in the living body, and is used as an additive of pharmaceuticals, foods, and feeding stuffs. Further, 5'-FMN is widely used as a starting material for flavine-adenine dinucleotide (hereinafter referred to as FAD) which is used as a therapeutic agent against vitamin $B_2$ deficiency.

Industrially, 5'-FMN is usually produced by reacting riboflavine with a phosphorylating agent such phosphoryl chloride. Accordingly, 5'-FMN produced contains impurities such as unreacted riboflavine, and 4'-FMN, riboflavine-4'-5'-cyclophosphate and riboflavine-phosphoric acid formed as by-products.

Since these impurities have analogous structures to that of 5'-FMN, it is difficult to separate the latter from the former. Especially, 4'-FMN has a very analogous structure to that of 5'-FMN, and therefore, it is extremely difficult to separate the latter from the former.

SUMMARY OF THE INVENTION

An object of the present invention is to provide a process for obtaining 5'-FMN containing a reduced amount of impurities from crude 5'FMN containing 4'-FMN.

According to the present invention, there can be obtained a fraction of 5'-FMN containing a reduced amount of impurities from eluates by subjecting crude 5'-FMN to chromatography using a column packed with a weakly basic anion-exchange resin having a skeleton of a crosslinked polyacrylic acid ester or polymethacrylic acid ester in which at least a part of the ester linkages thereof are converted into amide linkages represented by the following formula (1):

(1)

wherein $R_1$ represents a group denoted by

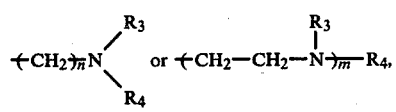

in which n is an integer of from 2 to 6, m is an integer of from 2 to 4, and $R_3$ and $R_4$ are each a hydrogen atom or an alkyl group having 1 to 6 carbon atoms; and $R_2$ is the same as defined in $R_1$ or represents a hydrogen atom or an alkyl group having 1 to 6 carbon atoms.

BRIEF DESCRIPTION OF THE DRAWINGS

FIGS. 1 and 2 each shows a chromatogram obtained by subjecting crude 5'-FMN to chromatography in accordance with the process of the present invention. In these figures, numerals 1, 2, 3, and 4 denote riboflavine, 5'-FMN, 4'-FMN, and X-component, respectively.

FIG. 3 shows a pH change of a column eluate when subjecting crude 5'-FMN to chromatography in accordance with the process of the present invention.

DETAILED DESCRIPTION OF THE INVENTION

The present invention is explained in more detail hereunder.

The present invention relates to a process for the purification of crude 5'-FMN containing 4'-FMN by means of column chromatography using as a column-filling material a specific weakly basic anion-exchange resin containing therein amide linkages. Examples of the weakly basic anion-exchange resin which can be used as a column-filling material are those having a structure in which at least a part of ester linkages of a crosslinked polyacrylic acid ester or polymethacrylic acid ester are converted into amide linkages represented by the following formula (1):

(1)

wherein $R_1$ represents a group denoted by the following formula (2) or (3):

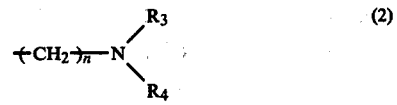
(2)

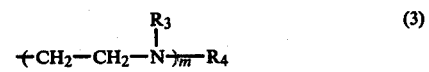
(3)

in which n is an integer of from 2 to 6, m is an integer of from 2 to 4, and $R_3$ and $R_4$ are each a hydrogen atom or an alkyl group having 1 to 6 carbon atoms; and $R_2$ is the same as defined in $R_1$ or represents a hydrogen atom or an alkyl group having 1 to 6 carbon atoms. In the formula (1), when $R_1$ represents a group denoted by the formula (2), then $R_1$ is usually a dimethylaminoalkyl group or a diethylaminoalkyl group, and $R_2$ is the same as defined in $R_1$ or a hydrogen atom. On the other hand, when $R_1$ represents a group denoted by the formula (3), then $R_2$ is usually a hydrogen atom, and $R_3$ and $R_4$ are each a hydrogen atom, a methyl group, an ethyl group, or a mixture thereof.

The above described weakly basic anion-exchange resin containing therein amido groups which is used in the present invention can be prepared by suspension polymerizing an acrylic acid ester, e.g., methyl acrylate and ethyl acrylate, or a corresponding methacrylic acid ester and a crosslinking agent, e.g., divinylbenzene in an aqueous medium by a known method to form a crosslinked copolymer which is subsequently reacted with an amine represented by the following formula (4):

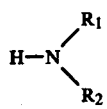

$$H-N\begin{matrix} R_1 \\ R_2 \end{matrix} \qquad (4)$$

wherein $R_1$ and $R_2$ are the same as defined in the formula (1), to thereby convert the ester linkages into amide linkages followed by, if desired, further alkylating the hydrogen atoms of the amino groups by treating with an alkylating agent. As the crude 5'-FMN to be subjected to chromatography, usually one obtained by reacting riboflavine, with a phosphorylating agent, e.g., phosphoryl chloride, is usable as it is. This crude 5'-FMN contains as impurities riboflavine polyphosphoric acid and other riboflavine derivatives and unreacted riboflavine in addition to 4'-FMN. Of course, crude 5'-FMN from which comparatively readily separable impurities such as unreacted riboflavine have preliminarily been removed can also be used.

Chromatography is carried out most simply by feeding a specified amount of a solution of crude 5'-FMN into the upper portion of a column packed with the above described weakly basic anion-exchange resin, followed by feeding thereinto a developer by a conventional method to develop the column. The column is preferably prepared by packing with the weakly basic anion-exchange resin in such a way that the height of the packed layer is in a range of from 0.5 to 10 m, preferably from 1 to 4 m. The weakly basic anion-exchange resin is preferably used in a form of carboxylic acid-loaded type treated with carboxylic acids such as formic acid, acetic acid, and carbonic acid.

When such carboxylic acid-loaded type resin is used, the adsorption band of 5'-FMN in the column will not spread and hence, 5'-FMN can be recovered from the column eluate in a high concentration. In contrast, when the carboxylic acid-loaded type resin is not used, it is preferred to use a mixture of one loaded with hydrochloric acid or other mineral acid and one of free type. However, when the resin is of completely mineral acid-loaded type or free type, it is generally difficult to achieve good separation. The crude 5'-FMN is fed into the column as a solution in a suitable solvent in such a way that its amount usually is in a range of from 0.5 to 20 g, preferably from 1 to 5 g, per liter of the weakly basic anion-exchange resin in the column. Usually, an aqueous solution of a salt is employed as the developer. The pH of the developer is preferably in a range of from 2 to 5. Examples of the salt include ammonium chloride, sodium chloride, potassium chloride and the like. Most simply, a 0.1 to 5 wt% sodium chloride aqueous solution is used as the developer; however, it is more preferable to use a buffer solution of sodium chloride aqueous solution having added thereto a buffering agent such as formic acid-sodium formate or acetic acid-sodium acetate. The flow rate of the developer is suitably in a range of from 0.05 to 5 m/hr.

When crude 5'-FMN is developed with a sodium chloride aqueous solution in accordance with the process of the present invention, riboflavine first flows out of the column, as shown in the accompanying drawings.

Subsequently 4'-FMN and a component considered to be either riboflavine-4'-5'-cyclophosphate or riboflavine-3'-monophosphate (this component being referred to as an X component) begin to flow out of the column, and finally, 5'-FMN begins to flow out of the column. The flowing-out curves of 4'-FMN and the X component and that of 5'-FMN overlap each other; however, since the curves differ from each other in the shape, purified 5'-FMN can be obtained by fractionating the latter portion of the flowing-out curve of 5'-FMN. Flowing-out of riboflabine-polyphosphoric acid delays considerably. The chromatography usually is carried out at room temperature (e.g., about 20° to 30° C.).

The present invention is explained more specifically with reference to Examples and Comparative Example, but it is not limited to the examples unless it is beyond the gist of the invention.

The weakly basic anion-exchange resin used in the Examples was prepared as follows:

Ethyl acrylate and industrial divinylbenzene (divinylbenzene content: 56%) were suspension polymerized in an aqueous medium by a conventional method to prepare a gel-type ethyl acrylate-divinylbenzene copolymer having a degree of crosslinking of 3%.

200 g of this copolymer which had been dried and 1000 g of N,N-dimethylpropylene diamine were charged in an autoclave, and the mixture was allowed to react at 190° C. for 20 hours. The reaction product was filtered off and sufficiently washed successively with water, 1N hydrochloric acid, water, a 1N sodium hydroxide aqueous solution, and water.

The weakly basic anion-exchange resin thus obtained had an ion-exchange capacity of 1.1 meq/g, a water content of 69%, and an average particle diameter of 350 μm.

The analysis of each component in the examples was carried out by high-speed liquid chromatography under the following conditions:

Column: μ-Bondapack C 18, manufactured by Waters Co., Ltd.
Eluant: 0.015M ammonium acetate solution of methanol-water (volume ratio=21:79)
Flow rate: 1.0 ml/min
Temperature: room temperature (i.e., about 20° to 30° C.)
Detection: UV 254 nm Under the foregoing conditions, components each having a retention time of 3,7,9,11, and 34 minutes were identified as riboflavine polyphosphoric acid, X component, 4'-FMN, 5'-FMN, and riboflavine, respectively. The concentrations are shown by converting the absorbance at UV 254 into that of 5'-FMN.

EXAMPLE 1

A free-type weakly basic anion-exchange resin was introduced into a large amount of a 1 wt% sodium chloride aqueous solution that had been adjusted to a pH of 3.8 with 1N hydrochloric acid, and the mixture was kept under stirring such that the resin and the aqueous solution reached an equilibrium state. 215 ml of the resin thus treated was packed into a glass tube having an inside diameter of 15 mm to provide a column for chromatography. Into this column was fed 172 ml of an aqueous solution of crude FMN containing 3540 mg/l of 5'-FMN, 635 mg/l of 4'-FMN, 300 mg/l of riboflavine, 110 mg/l of riboflavine polyphosphoric acid, and 420 mg/l of the X component considered to be either riboflavine-4'-5'-cyclophosphate or riboflavine-3'-monophosphate from the upper portion of the column at a flow rate of 0.25 m/hr. An aqueous solution containing 0.83 g/l of formic acid and 10 g/l of sodium chloride that had been adjusted to a pH of 3.8 with 1N sodium hydroxide was passed as a developer through the column at a flow rate of 0.25 m/hr. Thus, a chromatogram shown in FIG. 1 was obtained. The riboflavine polyphosphoric acid did not flow out of the column until 3 l of the developer passed through the column. In this example, all operations were conducted at room temperature (i.e., about 20° to 30° C.).

EXAMPLE 2

A free-type weakly basic anion-exchange resin was introduced into a large amount of a 0.018N formic acid aqueous solution that had been adjusted to a pH of 3.8 with 1N sodium hydroxide, and the mixture was kept under stirring such that the resin and the aqueous solution reached an equilibrium state. 430 ml of the resin thus treated was packed into a glass tube having an inside diameter of 15 mm to provide a column for chromatography.

Using this column, the chromatography of crude FMN was carried out in the same manner as in Example 1. Thus, a chromatogram shown in FIG. 2 was obtained. FIG. 3 shows the pH change of the eluate from the column.

After 4 ml of the same developer as used in Example 1 had been passed through the column, 0.5 l of 2N hydrochloric acid and 1 l of 1N sodium hydroxide were successively passed therethrough. Further, a 0.018N formic acid aqueous solution that had been adjusted to a pH of 3.8 with a 1N sodium hydroxide aqueous solution was passed through the column to thereby render the resin in a equilibrium state with the formic acid aqueous solution.

Using this column, the chromatography of crude FMN was carried out in the same manner as in Example 1. Thus, the similar chromatogram to that obtained in Example 1 was obtained.

COMPARATIVE EXAMPLE

The chromatography of crude FMN was carried out in the same manner as in Example 2 except that there were respectively used as a column-filling material Diaion WA30 (a registered trademark of Mitsubishi Chemical Industries Limited for a weakly basic anion-exchange resin containing therein dimethylbenzylamine-type functional radicals), Diaion PA408 (a registered trademark of Mitsubishi Chemical Industries Limited for a weakly basic anion-exchange resin containing therein dimethylbenzylethanolamine-type functional radicals), and Amberlite IRA458 (a registered trademark of Rhom & Haas Co. for a strongly basic anion-exchange resin containing therein N-{ω-(N',N',N'-trimethylammonium)alkyl}-amide-type functional radicals. As a result, however, the 5'-FMN was not substantially separated from the 4'-FMN. Further, the separation of the 5'-FMN from other impurities was poor.

While the invention has been described in detail and with reference to specific embodiments thereof, it will be apparent to one skilled in the art that various changes and modifications can be made therein without departing from the spirit and scope thereof.

What is claimed is:

1. A process for the purification of riboflavine-5'-monophosphate comprising subjecting crude riboflavine-5'-monophosphate containing riboflavine-4'-monophosphate to chromatography using a column packed with a weakly basic anion-exchange resin having a skeleton of a crosslinked polyacrylic acid ester or polymethacrylic acid ester in which at least a part of the ester linkages thereof are converted into amide linkages represented by the following formula (I):

wherein $R_1$ represents a group denoted by

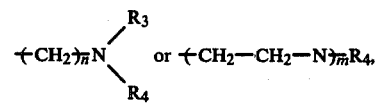

in which n is an integer of from 2 to 6, m is an integer of from 2 to 4, and $R_3$ and $R_4$ are each a hydrogen atom or an alkyl group having 1 to 6 carbon atoms; and $R_2$ is the same as defined in $R_1$ or represents a hydrogen atom or an alkyl group having 1 to 6 carbon atoms, to obtain a fraction of riboflavine-5'-monophosphate containing a reduced amount of riboflavine-4'-monophosphate from an eluate of the column.

2. The process as claimed in claim 1, wherein said weakly basic anion-exchange resin is in the form of a carboxylic acid-loaded type treated with carboxylic acids.

3. The process as claimed in claim 1, wherein said weakly basic anion-exchange resin is produced by suspension copolymerizing, in an aqueous medium, an alkyl ester of acrylic acid or methacrylic acid and a cross-linking agent to form a cross-linked copolymer and reacting the same with an amine represented by the following formula (4);

wherein $R_1$ and $R_2$ are the same as defined in formula (I), to convert the ester linkages into amide linkages, optionally followed by further alkylating the hydrogen atoms of the amino groups by treating with an alkylating agent.

4. The process as claimed in claim 3, wherein said alkyl ester is methyl acrylate or ethyl acrylate.

5. The process as claimed in claim 3, wherein said alkyl ester is methyl methacrylate or ethyl methacrylate.

6. The process as claimed in claim 3, wherein said cross-linking agent is divinyl benzene.

7. The process as claimed in claim 1, wherein said crude riboflavine-5'-monophosphate is a reaction product of riboflavine and a phosphorus oxidizing agent.

8. The process as claimed in claim 1, wherein said crude riboflavine-5'-monophosphate is dissolved in a solution and is passed through said column packed with said weakly basic anion-exchange resin and developed with an aqueous solution of a salt at pH 2 to 5 to obtain the fraction of riboflavine-5'-monophosphate.

9. The process as claimed in claim 8, wherein said developer is a buffer solution of aqueous sodium chloride.

10. The process as claimed in claim 3, wherein said weakly basic anion-exchange resin is produced by suspension copolymerizing ethyl acrylate and divinyl benzene in an aqueous medium and reacting the copolymer so produced with N,N'-dimethyl propylenediamine.

* * * * *